(12) United States Patent
Makkapati et al.

(10) Patent No.: US 9,776,016 B2
(45) Date of Patent: Oct. 3, 2017

(54) SYSTEM AND METHOD TO SELECTIVELY ILLUMINATE AN INFANT DURING PHOTOTHERAPY

(71) Applicant: KONINKLIJKE PHILIPS N.V., Eindhoven (NL)

(72) Inventors: Vishnu Vardhan Makkapati, Ongole (IN); Anil Shivram Raiker, Goa (IN); Shrutin Ulman, Bangalore (IN)

(73) Assignee: Koninklijke Philips N.V., Eindhoven (NL)

( * ) Notice: Subject to any disclaimer, the term of this patent is extended or adjusted under 35 U.S.C. 154(b) by 57 days.

(21) Appl. No.: 14/425,155

(22) PCT Filed: Sep. 2, 2013

(86) PCT No.: PCT/IB2013/058217
§ 371 (c)(1),
(2) Date: Mar. 2, 2015

(87) PCT Pub. No.: WO2014/037867
PCT Pub. Date: Mar. 13, 2014

(65) Prior Publication Data
US 2015/0217132 A1 Aug. 6, 2015

Related U.S. Application Data

(60) Provisional application No. 61/696,483, filed on Sep. 4, 2012.

(51) Int. Cl.
*A61N 5/06* (2006.01)
*A61G 11/00* (2006.01)

(52) U.S. Cl.
CPC ............ *A61N 5/0621* (2013.01); *A61G 11/00* (2013.01); *A61G 2203/44* (2013.01); *A61G 2203/46* (2013.01); *A61N 2005/0627* (2013.01); *A61N 2005/0637* (2013.01); *A61N 2005/0642* (2013.01); *A61N 2005/0652* (2013.01); *A61N 2005/0666* (2013.01)

(58) Field of Classification Search
CPC .................................................... A61N 5/0621
See application file for complete search history.

(56) References Cited

U.S. PATENT DOCUMENTS

| | | | |
|---|---|---|---|
| 2003/0233138 A1 | 12/2003 | Spooner | |
| 2006/0089546 A1* | 4/2006 | Mahony | A61B 5/0064 600/310 |
| 2007/0027510 A1* | 2/2007 | Rodrigues | A61N 5/0621 607/88 |

FOREIGN PATENT DOCUMENTS

| | | |
|---|---|---|
| WO | 2006135865 A2 | 12/2006 |
| WO | 2009073396 A1 | 6/2009 |
| WO | 2011153599 A1 | 12/2011 |

* cited by examiner

*Primary Examiner* — Eric D. Bertram (57) ABSTRACT

A system and method to selectively illuminate (part of) an infant during phototherapy uses an array of collimators and a set of light sources to control impingement of electromagnetic radiation on the infant.

18 Claims, 3 Drawing Sheets

SYSTEM AND METHOD TO SELECTIVELY ILLUMINATE AN INFANT DURING PHOTOTHERAPY

CROSS-REFERENCE TO PRIOR APPLICATIONS

This application is the U.S. National Phase application under 35 U.S.C. §371 of International Application No. PCT/IB2013/058217, filed on Sep. 2, 2013, which claims the benefit of U.S. Provisional Patent Application No. 61/696,483, filed on Sep. 4, 2012. These applications are hereby incorporated by reference herein.

The present disclosure pertains to systems and methods for providing phototherapy to an infant, and, in particular, to systems and methods that selectively illuminate part of an infant based on the location of the infant.

It is well known to treat infants, e.g. neonates, with phototherapy. An example of well-known phototherapy is jaundice treatment using blue light. It is well-known that the type of blue light that is effective for jaundice treatment may be undesirable when exposed for prolonged periods to the eyes of an infant.

Accordingly, it is an object of one or more embodiments of the present invention to provide a phototherapy system for an infant. The system comprises an array of collimators; a set of light sources, one or more sensors, and one or more processors configured to execute computer program modules. The set of light sources are configured and arranged such that, responsive to the phototherapy system being arranged in suitable proximity to an infant, electromagnetic radiation emitted by a subset of the set of light sources is guided through the array of collimators to impinge on the infant. The one or more sensors generate one or more output signals conveying information related to a location of the infant. The computer program modules comprise a location module configured to determine the location of an infant, wherein the determination is based on information from the one or more sensors, and a light module configured to control impingement of the electromagnetic radiation on the infant based on the determined location of the infant.

It is yet another aspect of one or more embodiments of the present invention to provide a method for phototherapy for an infant using a system that includes an array of collimators, a set of light sources being arranged in suitable proximity to an infant, and one or more sensors. The method comprises generating, by the one or more sensors, one or more output signals conveying information related to a location of the infant; determining the location of the infant based on the one or more output signals; emitting electromagnetic radiation by a subset of the set of light sources; guiding emitted electromagnetic radiation through the array of collimators to impinge on the infant; and controlling impingement of the electromagnetic radiation on the infant based on the determined location of the infant.

It is yet another aspect of one or more embodiments to provide a system configured to provide phototherapy to an infant. The system comprises means for generating one or more output signals conveying information related to a location of the infant, means for determining the location of the infant based on the one or more output signals, means for emitting electromagnetic radiation, an array of guiding means for guiding emitted electromagnetic radiation to impinge on the infant, and means for controlling impingement of the electromagnetic radiation on the infant based on the determined location of the infant.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
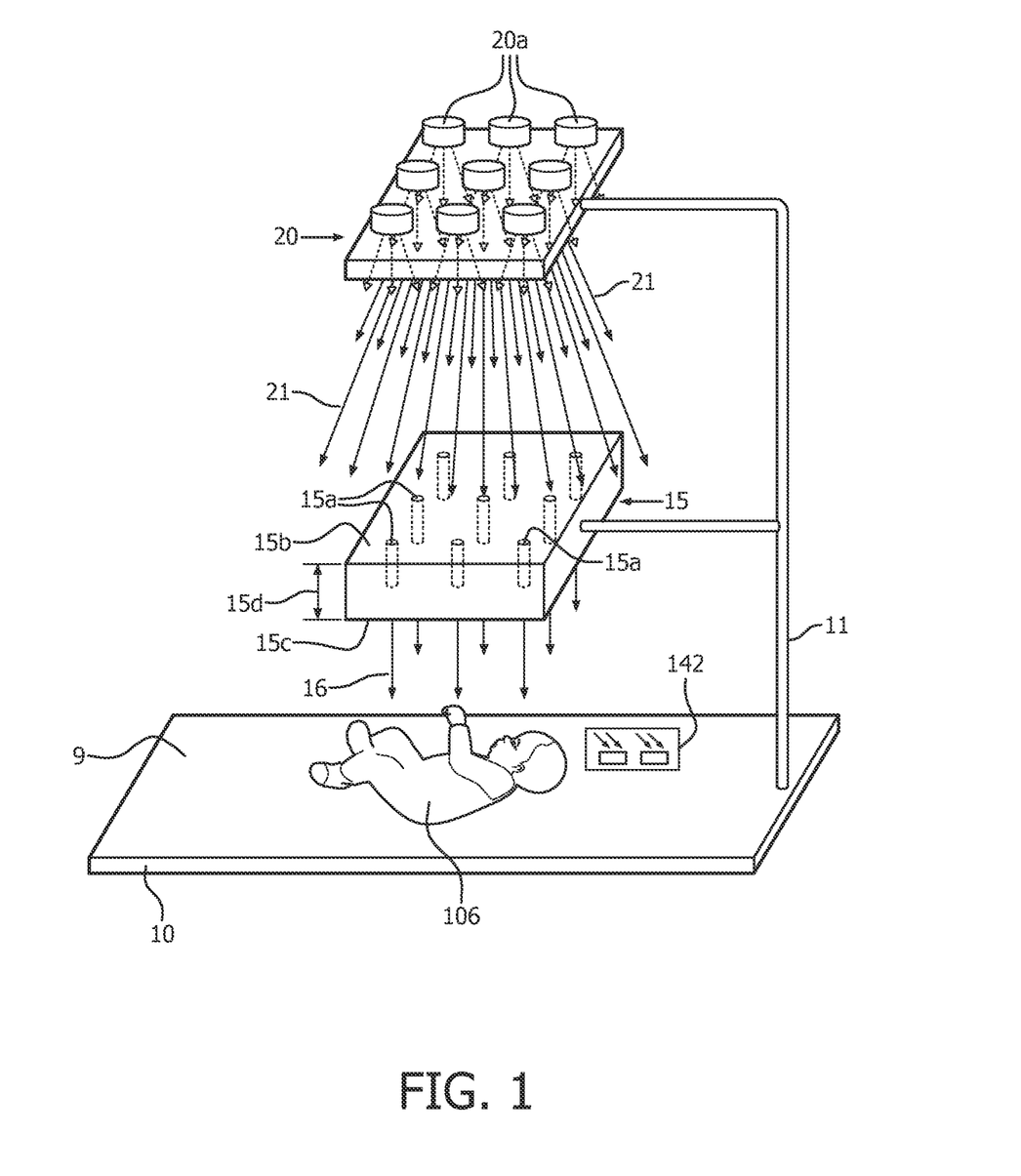
FIG. 1 illustrates a view of a phototherapy system in accordance with one or more embodiments.

FIG. 1 illustrates a view of a phototherapy system 10 in accordance with one or more embodiments. The view combines aspects from a side view and a view from an elevated position. System 10 may include one or more of an infant-supporting body 9, support structure 11, an array 15 of collimators 15a, one or more sensors 142, a set 20 of light sources 20a, and/or other components. Infant-supporting body 9 may be configured to support on infant 106, e.g. on a top-surface of infant-supporting body 9. Infant-supporting body 9 may engage infant 106 during use of system 10. Support structure 11 may be interchangeably referred to as a stand. Support structure 11 may be configured to carry set 20 of light sources 20a, array 15 of collimators 15a, and/or other components of system 10. The number of light sources 20a and collimators 15a depicted in FIG. 1 is exemplary, not intended to be limiting in any way, and these numbers do not need to match. In some embodiments, system 10 may include fewer light sources 20a than collimators 15a. The distance depicted in FIG. 1 between set 20 of light sources 20a and array 15 of collimators 15a is exemplary and not intended to be limiting in any way. In some embodiments, set 20 and array 15 may physically engage each other, be combined in one housing, and/or otherwise be placed in close proximity having a distance of less than about 1 inch, less than about 0.5 inch, and/or another distance. In some embodiments, the relative position of set 20 and array 15 may be manually and/or automatically adjustable. In some embodiments, system 10 may not include infant-supporting body 9 and/or support structure 11.

Phototherapy may be used to treat jaundice (or hyperbilirubinemia) by reducing the level of bilirubin. Effective and/or appropriate levels of phototherapy may be based on an infant's age, size, weight, and/or other physiological, environmental, and/or infant-specific parameters. Phototherapy may use electromagnetic radiation having a peak wavelength between, e.g., 460 nm and 500 nm, an emission spectrum ranging from, e.g., 400 nm to 520 nm, and preferably using a narrow bandwidth delivered at an irradiance of, e.g., 30-35 $\mu W/cm^2/nm$ to, e.g., up to 80% of an infant's body surface area (BSA). Phototherapy may potentially need to be kept from directly impinging on the eyes of the infant, e.g. by making the infant wear goggles. Exposure to the type of blue light that is effective for jaundice treatment may have side-effects for caregivers, including, but not limited to, headache, nausea, and/or vertigo.

System 10 in FIG. 1 may be configured to engage with and/or carry set 20 of light sources 20$a$, such that, responsive to activation of some or all of light sources 20$a$, electromagnetic radiation 21 emitted by light sources 20$a$ is guided through array 15 of collimators 15$a$. Individual collimators 15$a$ may include and/or form (reflective) tubes through which electromagnetic radiation, in particular the therapeutic blue light, is narrowed. As depicted by the non-parallel arrows accompanying electromagnetic radiation 21 in FIG. 1, emission by light sources 20$a$ may be a diverging beam of electromagnetic radiation. Array 15 and/or collimators 15$a$ may be oriented such that electromagnetic radiation 21 is guided from top-side 15$b$ to bottom-side 15$c$ across a depth 15$d$. As referred to herein, "narrow" may include causing the directions of motion (e.g. of electromagnetic particles) to become more aligned in a specific direction (interchangeably referred to as being collimated or parallelized) and/or causing the spatial cross-section of a beam of electromagnetic radiation to become smaller (e.g. by blocking, reflecting, deflecting, and/or absorbing electromagnetic radiation having an undesired characteristic or direction). Emitted electromagnetic radiation 21 may be narrowed, collimated, and/or parallelized by being guided through array 15 of collimators 15$a$, from top-side 15$b$ to bottom-side 15$c$ such that narrowed electromagnetic radiation 16 is emitted/guided from array 15 of collimators 15$a$ to impinge on infant 106 and thus provide phototherapy to infant 106. Narrowed electromagnetic radiation 16 may be parallel and/or diverging. In embodiments, cases, and/or circumstances where narrowed electromagnetic radiation 16 is diverging, the divergence is reduced with comparison to emitted electromagnetic radiation 21.

Infant 106 may be monitored while on or near system 10 or a component thereof, e.g. while undergoing phototherapy. In some embodiments, infant 106 may be monitored using one or more sensors 142.

One or more sensors 142 of system 10 in FIG. 1 may be configured to generate output signals conveying information related to the age, location, position, posture, size, weight, and/or status of infant 106, physiological, environmental, and/or infant-specific (medical) parameters related to infant 106, and/or other information. System 10 may use any of the generated output signals to monitor infant 106. In some embodiments, the conveyed information may be related to parameters associated with the state and/or condition of infant 106, the breathing of infant 106, the gas breathed by infant 106, the heart rate of infant 106, the respiratory rate of infant 106, vital signs of infant 106, including one or more temperatures, oxygen saturation of arterial blood ($SpO_2$), whether peripheral or central, and/or other parameters.

As a non-limiting example, one or more sensors 142 may generate one or more output signals conveying information related to a location of infant 106 on infant-supporting body 9, e.g. through stereoscopy. The location may be a three-dimensional location of the infant, a two-dimensional location of the infant, a location of a specific body part of the infant (e.g., eyes, arms, legs, a face, a head, a forehead, and/or other anatomical parts of the infant), a location of the infant as a whole, the presence of the infant, the posture of the infant, the orientation of the infant or one or more anatomical parts of the infant, relative spatial information pertaining to the infant or more or more anatomical parts of the infant, and/or other locations. In some embodiments, one or more sensors 142 may be configured to generate output signals conveying information related to whether the eyes of infant 106 are opened or closed, and/or which direction the eyes of infant 106 are facing. During phototherapy, it is preferred that emitted electromagnetic radiation from light sources 20$a$ substantially does not directly impinge on the eyes of infant 106. Sensors 142 may include one or more of a temperature sensor, one or more pressure/weight sensors, one or more light sensors, one or more electromagnetic (EM) sensors, one or more infra-red (IR) sensors, one or more still-image cameras, one or more video cameras, and/or other sensors and combinations thereof. For example, information related to the location of infant 106 on infant-supporting body 9 may be conveyed by output signals of a set or array of infra-red sensors, e.g. arranged around the periphery of infant-supporting body 9.

In some embodiments, sensors 142 may be configured to generate output signals conveying information related to a level of bilirubin in infant 106. Such sensors may for example be used to perform interstitial fluids bilirubin measurements.

The illustration of sensor 142 including two members in FIG. 1 is not intended to be limiting. System 10 may include one or more sensors. The illustration of a particular symbol or icon for sensor 142 in FIG. 1 is exemplary and not intended to be limiting ion any way. Resulting signals or information from one or more sensors 142 may be transmitted to processor 110, user interface 120, electronic storage 130, and/or other components of system 10. This transmission can be wired and/or wireless.

Monitoring of infant 106 may be based on one or more sensors 142 and/or any of the related parameters described herein. Monitoring and/or measuring may be used as a contact-less, non-invasive means to obtain information. "Contact-less" refers to either refraining from the use of adhesives (e.g. on the skin of infant 106) and/or refraining from direct skin contact in the context of this disclosure.

One or more light sources 20$a$ of system 10 in FIG. 1 may be configured such that electromagnetic radiation 21 emitted by one or more light sources 20$a$ is guided through array 15 of collimators 15$a$. Individual light sources 20$a$ may include one or more of a light-emitting diode (LED), organic LED (OLED), and/or other source of electromagnetic radiation, in particular non-parallel or non-focused electromagnetic radiation. In some embodiments, individual light sources 20$a$ may have a level of irradiance of about 2000 $\mu W/cm^2/nm$. Electromagnetic radiation 21 may not be narrow or focused in the way, e.g., a laser would be. Rather, electromagnetic radiation 21 emitted by light sources 20$a$ may have a wide angle (e.g. more than about 10 degrees, about 15 degrees, about 20 degrees, and/or another number of degrees). Alternatively, and/or simultaneously, electromagnetic radiation 21 may be diverging to a predetermined degree (e.g. such that the diameter of the cross-section of a cone of electromagnetic radiation emitted from an individual light source 20a is more than about 3 cm, about 5 cm, about 10 cm, about 25 cm, about 50 cm, and/or other diameters at a distance less than 1 m from the individual light source 20a, and/or other combinations of a diameter of a cross-section of a cone and distance that correspond to a similar degree of diverging electromagnetic radiation). Alternatively, and/or simultaneously, electromagnetic radiation 21 may be diffuse, and/or otherwise not sufficiently narrow to accurately control and/or prevent impingement of electromagnetic radiation in the face and/or eyes of infant 106. Light sources 20a may be arranged in a regular pattern, irregular pattern, or combination of both. For example, light sources 20a may be arranged in a regular grid.

Light sources 20a of system 10 may be configured to have a controllable level of intensity (e.g. denoted by a percentage of the maximum available level of intensity for an individual light source), a controllable direction and/or angle of illumination (as depicted by multiple directions of electromagnetic radiation 21 for individual light sources 20a in various figures including FIG. 1), a controllable selection of illumination spectra, and/or other controllable illumination characteristics and/or illumination parameters. For example, illumination parameters of a light source 20a may be controlled by adjusting optical components within the light source, including, but not limited to, one or more of refractive components, reflective components, lenses, mirrors, filters, polarizers, diffraction gradients, optical fibers, and/or other optical components. Individual light sources 20a may be controlled such that only part of (the exposed skin of) infant 106 is illuminated. Particularly, part of (the exposed skin of) infant 106 that is not at or near the eyes of infant 106. As used herein, "illumination" of infant 106 may be interchangeably referred to as impingement of electromagnetic radiation on infant 106.

Note that electromagnetic radiation emitted by real-world light sources, as opposed to theoretical models of light sources, may have a non-deterministic distribution of its intensity and/or (beam) direction, at least for practical applications of phototherapy and/or digital image processing. Note furthermore that guiding, reflecting, and/or scattering a beam of electromagnetic radiation may be considered a stochastic event governed by a probability distribution. Nonetheless, electromagnetic radiation may be considered to substantially directly impinge on or near a particular surface and/or location if at least about 90%, at least about 95%, about 99%, and/or another percentage of the emitted radiation directly so impinges.

Individual collimators 15a may be configured such that a cone of narrowed electromagnetic radiation 16, responsive to being guided through the individual collimator 15a, has a cross-section perpendicular to the optical path of the beam of electromagnetic radiation with a predetermined diameter at a predetermined distance from a point of disengagement from the individual collimator 15a. As used in this disclosure, the "diameter of the cone" of (a beam of) electromagnetic radiation" includes "the diameter of a cross-section of the cone perpendicular to the optical path of (the beam of) electromagnetic radiation." The point of disengagement may be defined as the point or area where electromagnetic radiation passed bottom-side 15c of the individual collimator 15a, and/or another point such that the individual collimator 15a no longer narrows, collimates, parallelizes, and/or focuses the electromagnetic radiation past the point of disengagement. The predetermined diameter of the cross-section of the cone of narrowed electromagnetic radiation may be about 3 cm, about 1 inch, about 2 cm, about ½ inch, about 0.5 cm, and/or another appropriate diameter. In some embodiments, the predetermined diameter may be designed such that cones of neighboring collimators 15a have no or little overlap as they impinge on infant 106. The predetermined distance from the point of disengagement may be about 10 cm, about 20 cm, about 30 cm, about 40 cm, about 50 cm, about 60 cm, about 70 cm, about 80 cm, about 90 cm, about 1 m, and/or other appropriate distances. The predetermined distance may be manually and/or automatically adjustable.

Depth 15d of array 15 and/or collimators 15a may be about 5 cm, about 10 cm, about 15 cm, about 20 cm, and/or another appropriate depth such that, given the distance between the point of disengagement and the area of impingement on infant 106, the diameter of the cross-section of the cone of electromagnetic radiation from an individual collimator 15a has appropriate dimensions as described herein. Note that collimators 15a that are included in array 15 need not all have the same depth and/or the same other characteristics. In some embodiments, depth 15d may be adjustable manually and/or automatically, for example based on the distance between the point of disengagement and the area of impingement on infant 106 (and/or infant-supporting body 9), or the distance between set 20 of light sources 20a and array 15 or collimators 15a, and/or any combination based on one or more of these distances. For example, increasing depth 15d may cause the diameter of the cross-section of the cone of electromagnetic radiation from an individual collimator 15a to decrease correspondingly, within a certain operating range. In other words, the beam of narrowed electromagnetic radiation 16 may in such a case be narrower, responsive to depth 15d being increased.

Figure 2:
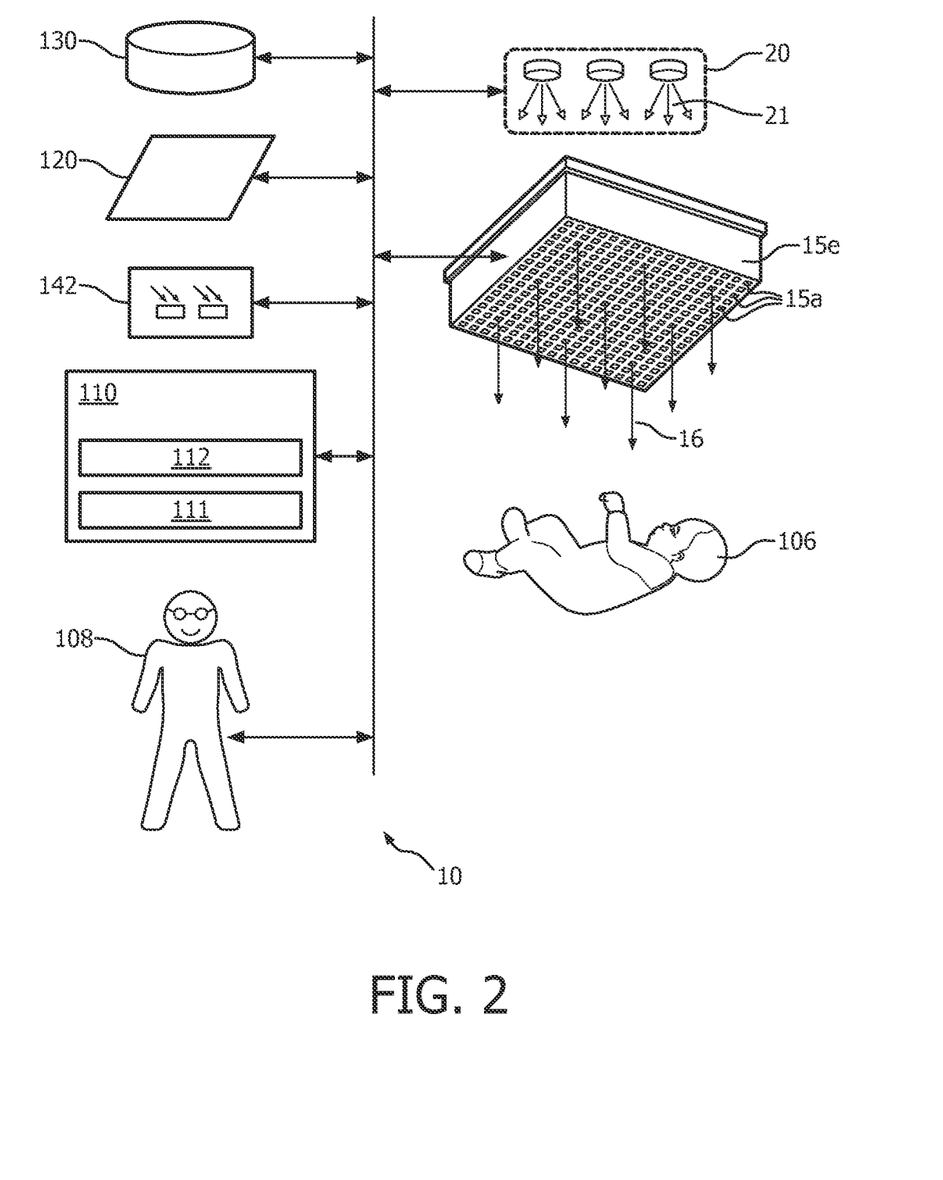
FIG. 2 schematically illustrates a phototherapy system in accordance with one or more embodiments.

FIG. 2 schematically illustrates a phototherapy system 10 in accordance with one or more embodiments. In addition to the previously listed components for system 10, in some embodiments, system 10 may include a user interface 120, electronic storage 130, one or more processors 110, a location module 111, a light module 112, and/or other components. The functionality of array 15e of collimators 15a in FIG. 2 (viewed from the bottom) is substantially similar to the functionality of array 15 of collimators 15a in FIG. 1, with the notable difference that array 15e in FIG. 2 includes a larger number of individual collimators 15a. The number of collimators 15a depicted in FIG. 2 is exemplary and not intended to be limiting in any way.

User interface 120 of system 10 in FIG. 2 may be configured to provide an interface between system 10 and a user (e.g., user 108, a caregiver, a healthcare provider, a therapy decision-maker, etc.) through which the user can provide information to and/or receive information from system 10. This enables data, results, and/or instructions and any other communicable items, collectively referred to as "information," to be communicated between the user and system 10. An example of information that may be conveyed to user 108 is a report detailing the changes in monitored vital signs throughout a period during which infant 106 is present near system 10 or undergoing (photo-) therapy. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 by user interface 120 in the form of auditory signals, visual signals, tactile signals, and/or other sensory signals, or any combination thereof.

By way of non-limiting example, user interface 120 may include a radiation source capable of emitting light. The radiation source may include, for example, one or more of at least one LED, at least one light bulb, a display screen, and/or other sources. User interface 120 may control the radiation source to emit light in a manner that conveys information to user 108.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 10 from removable storage (e.g., a smart card, a flash drive, a removable disk, etc.) that enables the user(s) to customize the implementation of system 10. Other exemplary input devices and techniques adapted for use with system 10 as user interface 120 include, but are not limited to, an RS-232 port, RF link, an IR link, modem (telephone, cable, Ethernet, internet or other). In short, any technique for communicating information with system 10 is contemplated as user interface 120.

Electronic storage 130 of system 10 in FIG. 2 comprises electronic storage media that electronically stores information. The electronic storage media of electronic storage 130 may include one or both of system storage that is provided integrally (i.e., substantially non-removable) with system 10 and/or removable storage that is removably connectable to system 10 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 10 to function properly. For example, electronic storage 130 may record or store information related to the provided phototherapy, and/or other information. Electronic storage 130 may be a separate component within system 10, or electronic storage 130 may be provided integrally with one or more other components of system 10 (e.g., processor 110).

Processor 110 of system 10 in FIG. 2 is configured to provide information processing capabilities in system 10. As such, processor 110 includes one or more of a digital processor, an analog processor, a digital circuit designed to process information, an analog circuit designed to process information, and/or other mechanisms for electronically processing information. Although processor 110 is shown in FIG. 2 as a single entity, this is for illustrative purposes only. In some implementations, processor 110 includes a plurality of processing units.

As is shown in FIG. 2, processor 110 is configured to execute one or more computer program modules. The one or more computer program modules include one or more of a parameter determination module, a location module 111, a light module 112, and/or other modules. Processor 110 may be configured to execute modules 111 and/or 112 by software; hardware; firmware; some combination of software, hardware, and/or firmware; and/or other mechanisms for configuring processing capabilities on processor 110.

It should be appreciated that although modules 111 and 112 are illustrated in FIG. 2 as being co-located within a single processing unit, in implementations in which processor 110 includes multiple processing units, one or more of modules 111 and 112 may be located remotely from the other modules. The description of the functionality provided by the different modules 111 and/or 112 described below is for illustrative purposes, and is not intended to be limiting, as any of modules 111 and/or 112 may provide more or less functionality than is described. For example, one or more of modules 111 and 112 may be eliminated, and some or all of its functionality may be provided by other ones of modules 111 and 112. Note that processor 110 may be configured to execute one or more additional modules that may perform some or all of the functionality attributed below to one of modules 111 and/or 112.

A parameter determination module of system 10 (not shown) may be configured to determine one or more status parameters, medical parameters, and/or other parameters from output signals generated by sensor(s) 142. Parameters may be related to an infant's age, size, volume, weight, and/or other physiological, environmental, and/or infant-specific parameters. One or more status parameters may be related to a determined location of infant 106. One or more medical parameters may be related to monitored vital signs of infant 106, and/or other medical parameters of infant 106. Other parameters may be related to the environment near system 10, such as, e.g., air temperature. Some or all of this functionality may be incorporated or integrated into other computer program modules of processor 110.

Location module 111 of system 10 in FIG. 2 may be configured to determine a location of infant 106 (and/or anatomical parts of infant 106). Note that a location may include one or more of a three-dimensional location of the infant, a two-dimensional location of the infant, a location of a specific body part of the infant (e.g., eyes, arms, legs, a face, a head, a forehead, and/or other anatomical parts of the infant), a location of the infant as a whole, the presence of the infant, the posture of the infant, the orientation of the infant or one or more anatomical parts of the infant, relative spatial information pertaining to the infant or more or more anatomical parts of the infant, and/or other locations. The determination by location module 111 may be based on information from one or more sensors 142, such as information from, e.g., one or more weight sensors, and/or through stereoscopy using one or more cameras. In some embodiments, location module 111 may be configured to determine in which area (and/or in which posture and/or orientation) exposed skin of infant 106, e.g. the head or feet of the infant, is currently located, such that light sources 20a may be controlled accordingly. Note that phototherapy through clothing or a diaper may be ineffective. In some embodiments, location module 111 may be configured to determine the location of, e.g., clothing and/or a diaper of infant 106.

In some embodiments, location module 111 may be configured to determine whether infant 106 is in a supine position. In some embodiments, location module 111 may be configured to determine in which direction the eyes of infant 106 are facing. Location module 111 may be configured to determine whether an alarm and/or notification is warranted due to a mismatch in provided and/or recommended phototherapy vs. one or more of a determined presence, position, posture, and/or orientation of infant 106. Such an alarm and/or notification may, e.g., be presented via user interface 120. Alternatively, and/or simultaneously, the provided phototherapy may be adjusted automatically, e.g. by controlling light sources 20*a*, responsive to a change in the determined presence, position, posture, and/or orientation of infant 106. Determinations by location module 111 may be used in other components of system 10.

In some embodiments, location module 111 may be configured to determine which light sources from the set of light sources 20*a*1 are in position to effectively provide phototherapy to infant 106, e.g. through using information conveyed by one or more imaging sensors. One or more imaging sensors, or cameras, may be arranged to capture output signals conveying visual information related to orientation location of infant 106. For example, a camera may capture an image of a top-view of infant 106. A lens (or other constituent component of a camera along the path from visual information to captured image) may insert, add, and/or superimpose a grid in/to/on the captured image. Alternatively, and/or simultaneously, a component external to the imaging sensor may be used to add grid information the captured image. For example, a grid may be depicted on a top-surface of an infant-supporting body. Such a grid may correspond in some predetermined and/or known fashion to either one or both of set 20 of light sources 20*a* and/or array 15 of collimators 15*a*, as described in relation to FIG. 1. One or more determinations by location module 111 may be based on grid information and/or the captured image.

In some embodiments, location module 111 may be configured to determine a target subset of light sources 20*a* that would contribute most and/or significantly to impingement of electromagnetic radiation on or near, e.g., the face or eyes of infant 106. In the context of contributing to impingement, "most" may be interpreted as "more than one or more other light sources 20*a*" and "significantly" may be interpreted as "more than a predetermined amount of electromagnetic radiation," wherein the predetermined amount of electromagnetic radiation may be quantified in various ways, including an irradiance of about 10, about 20, about 30, about 40, about 50 $\mu W/cm^2/nm$, and/or other levels of irradiance. The term "on or near the face or eyes" may be interpreted as "within a predetermined distance from the face or eyes," wherein the predetermined distance may be about 1 cm, 2 cm, 1 inch, 5 cm, 2 inches, and/or other distances as appropriate to substantially prevent impingement of electromagnetic radiation in the eyes on an infant in manners known to be medically undesirable.

Light module 112 of system 10 in FIG. 2 may be configured to control impingement of electromagnetic radiation on infant 106 based on the location of infant 106. Controlling impingement may include controlling one or more light sources 20*a* based on the determined location of infant 106 such that electromagnetic radiation emitted by one or more light sources 20*a* provides phototherapy for infant 106. Control by light module 112 may be based on individual light sources, one or more subsets of light sources, one or more groups of light sources, one or more rows and/or columns of light sources, and/or any combination thereof. Control by light module 112 may include control of the controllable level of intensity, the controllable direction and/or angle of illumination, the controllable selection of illumination spectra, and/or other controllable illumination characteristics and/or illumination parameters of one or more light sources 20*a*. Control by light module 112 may be based on information from location module 111.

In some embodiments, controlling impingement by light module 112 may include adjusting modifiable physical/mechanical structures, e.g. apertures, in or near individual collimators 15*a* to block or partially block electromagnetic radiation being guided through array 15. Alternatively, and/or simultaneously, a structure or object placed between set 20 of light sources 20*a* and array 15 of collimators 15*a* may accomplished the same functionality. For example, an array of liquid crystals, such as may be included in a liquid crystal display (LCD), may be selectively controlled to adjust how much electromagnetic radiation passes through (e.g. in the direction from set 20 to array 15). The granularity of control may be configured to match collimators 15*a*, such that electromagnetic radiation guided through individual collimators may be controlled individually.

Light sources 20*a* that contribute most or significantly to impingement of electromagnetic radiation on or near, e.g., the face or eyes of infant 106, may be adjusted and/or turned down and/or off. Alternatively, and/or simultaneously, light sources 20*a* that would emit radiation substantially on an area of infant 106 where no bare skin is exposed, may be adjusted and/or turned down and/or off. Adjustments may include one or more of turning individual light sources or groups of light sources off and/or down, changing operational parameters of individual light sources or groups of light sources such that the level of impinging electromagnetic radiation is affected and/or reduced), and/or other adjustments. Light sources 20*a* that are determined to not be in position to effectively provide phototherapy for infant 106 may be controlled and/or adjusted accordingly.

In some embodiments, light module 112 may be configured to adjust one or more settings of a particular target subset of light sources 20*a*, such as, e.g., a target subset of light sources 20*a* that is determined by location module 11 as described above. In doing so, light module 112 may control impingement of electromagnetic radiation on or near the face or eyes of infant 106.

Monitoring of the movements and changing positions of infant 106 may be used by light module 112 to adjust one or more light sources in keeping with the multiple goals of providing effective phototherapy to infant 106, and keeping electromagnetic radiation out of the eyes of infant 106.

System 10 may be configured to determine a recommended phototherapy regimen for infant 106. A phototherapy regimen may be based on one or more of information related to the size/volume/weight of infant 106, information related to the age of infant 106, information related to previously administered phototherapy to infant 106, information related to medical parameters pertaining to the status of infant 106 (e.g. bilirubin measurements), stated and/or provided information from a user 108 or caregiver, clinician input, guidelines, charts, and/or other information. The recommended phototherapy regimen may in turn be used as a basis for operations and/or adjustments by light module 112.

Figure 3:
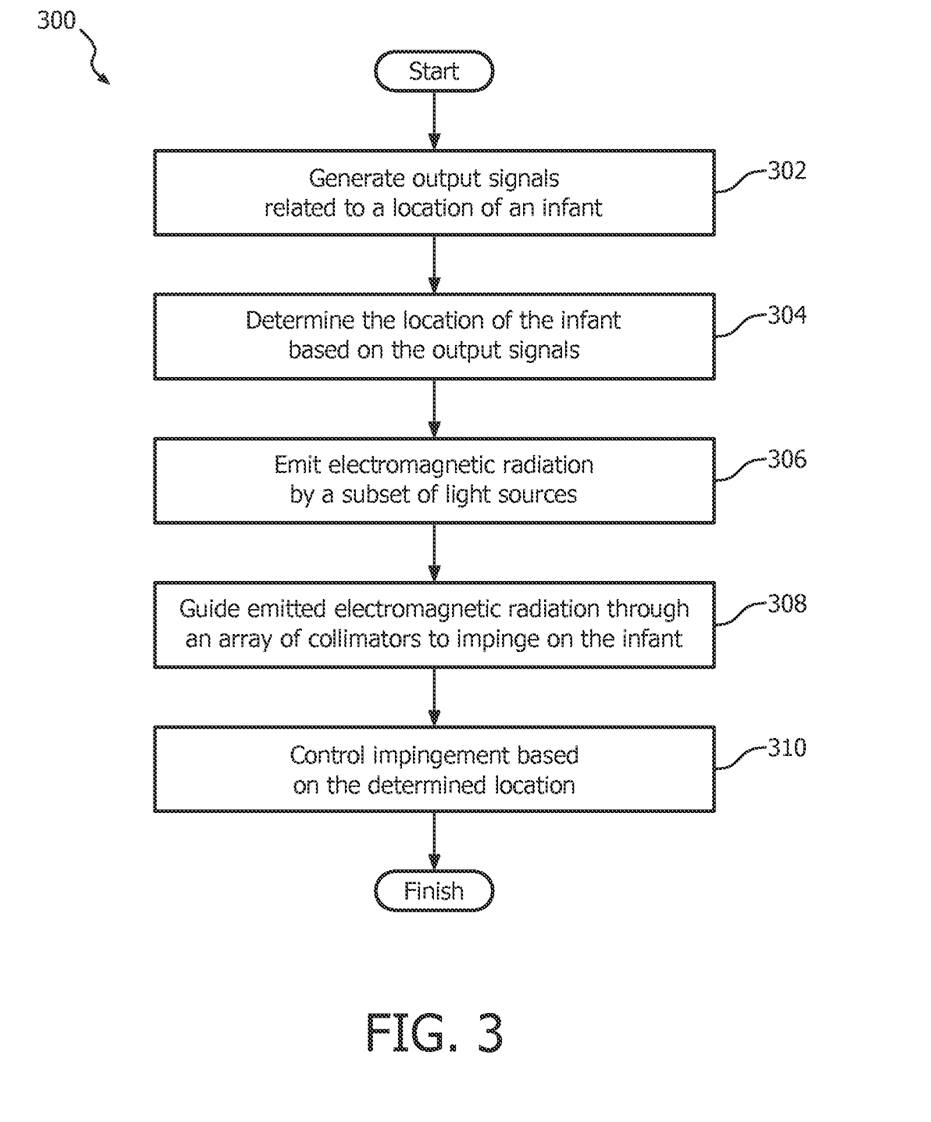
FIG. 3 illustrates a method for providing phototherapy in accordance with one or more embodiments.

FIG. 3 illustrates a method 300 for providing phototherapy to an infant. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting.

In some embodiments, method 300 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, one or more output signals conveying information related to a location of the infant are generated by the one or more sensors. In some embodiments, operation 302 is performed by one or more sensors the same as or similar to sensors 142 (shown in FIG. 1 and described herein).

At an operation 304, the location of the infant is determined based on the one or more output signals. In some embodiments, operation 304 is performed by a location module the same as or similar to location module 111 (shown in FIG. 2 and described herein).

At an operation 306, electromagnetic radiation is emitted by a subset of the set of light sources. In some embodiments, operation 306 is performed by light sources the same as or similar to light sources 20a (shown in FIG. 1 and described herein).

At an operation 308, emitted electromagnetic radiation is guided through the array of collimators to impinge on the infant. In some embodiments, operation 308 is performed by collimators the same as or similar to collimators 15a (shown in FIG. 1 and described herein).

At an operation 310, impingement of the electromagnetic radiation on the infant is controlled based on the determined location of the infant. In some embodiments, operation 310 is performed by a lighting module the same as or similar to lighting module 112 (shown in FIG. 2 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A phototherapy system for an infant, the system comprising:
an array of collimators;
a set of light sources, wherein the set of light sources are configured and arranged such that, responsive to the phototherapy system being arranged in suitable proximity to an infant, electromagnetic radiation emitted by a subset of the set of light sources is guided through the array of collimators to impinge on the infant, wherein individual ones of the collimators include a reflective tube configured to guide the electromagnetic radiation, and wherein the set of light sources and the array of collimators are spatially separated;
one or more sensors that generate one or more output signals conveying information related to a location of the infant; and
one or more processors configured to execute computer program modules, the computer program modules comprising:
a location module configured to determine the location of an infant, wherein the determination is based on information from the one or more sensors; and
a light module configured to control impingement of the electromagnetic radiation on the infant by selectively illuminating one or more individual ones of the collimators based on the determined location of the infant.

2. The system of claim 1, wherein the one or more sensors include a camera.

3. The system of claim 1, the infant having a face, wherein the location module is configured to determine a target subset of light sources that would contribute most to impingement of electromagnetic radiation on or near the face of the infant, and wherein the light module is configured to control impingement of the electromagnetic radiation on or near the face of the infant by adjusting one or more settings of the target subset of light sources.

4. The system of claim 1, further comprising one or more apertures disposed proximate to the array of collimators, wherein the one or more apertures are configured to control impingement of the electromagnetic radiation on the infant.

5. The system of claim 4, wherein the one or more apertures are individually adjustable to block or partially block the electromagnetic radiation based on the determined location of the infant.

6. A phototherapy system for an infant, the system comprising:
an array of collimators;
a set of light sources, wherein the set of light sources are configured and arranged such that, responsive to the phototherapy system being arranged in suitable proximity to an infant, electromagnetic radiation emitted by a subset of the set of light sources is guided through the array of collimators to impinge on the infant, wherein individual ones of the collimators include a reflective tube configured to guide the electromagnetic radiation, and wherein the set of light sources and the array of collimators are spatially separated;
one or more sensors that generate one or more output signals conveying information related to a location of the infant; and
one or more processors configured to execute computer program modules, the computer program modules comprising:
a location module configured to determine the location of an infant, wherein the determination is based on information from the one or more sensors; and
a light module configured to control impingement of the electromagnetic radiation on the infant by selectively illuminating one or more individual ones of the collimators based on the determined location of the infant, wherein the array of collimators is configured such that a cross-section of a cone of electromagnetic radiation guided through an individual collimator is less than 3 cm in diameter at distances less than 1 m from a point of disengagement from the individual collimator.

7. A method of providing phototherapy to an infant with a system, the system including one or more processors, one or more sensors, a set of light sources, and an array of collimators, the method comprising:
generating, by the one or more sensors, one or more output signals conveying information related to a location of an infant;
determining, by the one or more processors the location of the infant based on the one or more output signals;
emitting electromagnetic radiation by a subset of the set of light sources; and
guiding emitted electromagnetic radiation through the array of collimators to impinge on the infant, wherein individual ones of the collimators include a reflective tube configured to guide electromagnetic radiation, and wherein the set of light sources and the array of collimators are spatially separated.

8. The method of claim 7, wherein the one or more sensors include a camera.

9. The method of claim 7, the infant having a face, the method further comprising:
determining a target subset of light sources that would contribute most to impingement of electromagnetic radiation on or near the face of the infant,
wherein controlling the impingement of the electromagnetic radiation on the infant includes controlling impingement on or near the face of the infant by adjusting one or more settings of the target subset of light sources.

10. The method of claim 7, further comprising controlling impingement of the electromagnetic radiation on the infant with one or more apertures disposed proximate to the array of collimators.

11. The method of claim 10, wherein controlling impingement of the electromagnetic radiation on the infant includes individually adjusting the one or more apertures to block or partially block the electromagnetic radiation based on the determined location of the infant.

12. A method of providing phototherapy to an infant with a system, the system including one or more processors, one or more sensors, a set of light sources, and an array of collimators, the method comprising:
generating, by the one or more sensors, one or more output signals conveying information related to a location of an infant;
determining, by the one or more processors the location of the infant based on the one or more output signals;
emitting electromagnetic radiation by a subset of the set of light sources; and
guiding emitted electromagnetic radiation through the array of collimators to impinge on the infant, wherein individual ones of the collimators include a reflective tube configured to guide electromagnetic radiation, wherein an individual collimator from the array of collimators is configured such that a cross-section of a cone of electromagnetic radiation guided through the individual collimator is less than 3 cm in diameter at distances less than 1 m from a point of disengagement from the individual collimator, and wherein the set of light sources and the array of collimators are spatially separated.

13. A system configured to provide phototherapy to an infant, the system comprising:
means for generating one or more output signals conveying information related to a location of the infant;
means for determining the location of the infant based on the one or more output signals;
means for emitting electromagnetic radiation; and
an array of guiding means for guiding emitted electromagnetic radiation to impinge on the infant, wherein individual ones of the guiding means include a reflective tube configured to guide the electromagnetic radiation, and wherein the means for emitting electromagnetic radiation and the array of guiding means are spatially separated.

14. The system of claim 13, wherein one or more of the one or more output signals are generated by a camera.

15. The system of claim 13, the infant having a face, wherein the means for determining the location of the infant is further configured to determine a target subset of light sources that would contribute most to impingement of electromagnetic radiation on or near the face of the infant, and wherein the means for controlling the impingement of the electromagnetic radiation on the infant controls impingement on or near the face of the infant by adjusting one or more settings of the target subset of light sources.

16. The system of claim 13, further comprising means for controlling impingement of the electromagnetic radiation on the infant, the means for controlling impingement disposed proximate to the array of guiding means.

17. The system of claim 16, wherein the means for controlling impingement includes one or more apertures are individually adjustable to block or partially block the electromagnetic radiation based on the determined location of the infant.

18. A system configured to provide phototherapy to an infant, the system comprising:
means for generating one or more output signals conveying information related to a location of the infant;
means for determining the location of the infant based on the one or more output signals;
means for emitting electromagnetic radiation; and
an array of guiding means for guiding emitted electromagnetic radiation to impinge on the infant, wherein individual ones of the guiding means include a reflective tube configured to guide the electromagnetic radiation, wherein an individual guiding means is configured such that a cross-section of a cone of electromagnetic radiation guided through the individual guiding means is less than 3 cm in diameter at distances less than 1 m from a point of disengagement from the individual guiding means, and wherein the means for emitting electromagnetic radiation and the array of guiding means are spatially separated.

* * * * *